United States Patent
Parks et al.

(10) Patent No.: US 8,042,688 B2
(45) Date of Patent: Oct. 25, 2011

(54) COMBINED DRAPE AND CARRYING BAG UNIT

(75) Inventors: William Parks, Lawrenceville, GA (US); Louis Malice, Marietta, GA (US)

(73) Assignee: Endochoice, Inc., Alpharetta, GA (US)

(*) Notice: Subject to any disclaimer, the term of this patent is extended or adjusted under 35 U.S.C. 154(b) by 0 days.

(21) Appl. No.: 12/665,557

(22) PCT Filed: Aug. 27, 2008

(86) PCT No.: PCT/US2008/074395
§ 371 (c)(1),
(2), (4) Date: Dec. 18, 2009

(87) PCT Pub. No.: WO2009/032670
PCT Pub. Date: Mar. 12, 2009

(65) Prior Publication Data
US 2010/0187136 A1    Jul. 29, 2010

Related U.S. Application Data

(60) Provisional application No. 60/967,018, filed on Aug. 31, 2007, provisional application No. 61/052,594, filed on May 12, 2008.

(51) Int. Cl.
*A61B 19/02* (2006.01)
*B65D 33/28* (2006.01)
*A61F 13/15* (2006.01)

(52) U.S. Cl. ............ 206/438; 128/849; 206/363; 383/4; 383/75; 604/358; 604/386

(58) Field of Classification Search .......... 206/363–370, 206/438–441, 570–572; 128/849–856; 383/4, 383/72–76; 604/357–359, 389
See application file for complete search history.

(56) References Cited

U.S. PATENT DOCUMENTS

| | | | |
|---|---|---|---|
| 3,475,767 A * | 11/1969 | Friesen et al. | 383/75 |
| 3,561,439 A * | 2/1971 | Bayer | 128/853 |
| 3,650,267 A * | 3/1972 | Anderson | 128/853 |
| 4,738,545 A | 4/1988 | Westgor | |

(Continued)

OTHER PUBLICATIONS

International Search Report for International Application No. PCT/US2008/074395 mailed Oct. 31, 2008.

*Primary Examiner* — Bryon Gehman
(74) *Attorney, Agent, or Firm* — Pearl Cohen Zedek Latzer, LLP

(57) ABSTRACT

The present invention provides a combination drape and carrying bag unit including a singular sheet or plurality of joined sheet of pliable materials, both permeable and impermeable, of size to define a mat to accommodate a working medical procedural area thereon, upon which may be placed in single or combination, medical equipment and patient. The sheet has a drawstring casing extending about its periphery. The casing has openings therein on opposite sides of the mat and a drawstring is received in the drawstring casing and is of size to extend continuously about the periphery of the sheet when it defines a mat. The drawstring is slidably received in the drawstring casing so that when portions of the drawstring are pulled out of the drawstring casing through the openings, the periphery of the sheet forms gathers adjacent the casing to permit the periphery to reduce in size whereby the unit forms a carrying bag. Those portions of the drawstring which are pulled out of the casing may be secured together adjacent the openings to form a handle for the carrying bag.

15 Claims, 5 Drawing Sheets

U.S. PATENT DOCUMENTS

| | | | | |
|---|---|---|---|---|
| 4,800,677 | A | * | 1/1989 | Mack .............................. 604/359 |
| 4,923,453 | A | * | 5/1990 | Bullard, Jr. .................... 128/855 |
| 4,931,052 | A | * | 6/1990 | Feldman ......................... 383/75 |
| 5,151,314 | A | * | 9/1992 | Brown ........................... 128/849 |
| 5,464,024 | A |  | 11/1995 | Mills et al. |
| 5,476,456 | A | * | 12/1995 | Rankin et al. ................. 604/358 |
| 5,816,253 | A | * | 10/1998 | Sosebee ........................ 128/849 |
| 5,988,172 | A | * | 11/1999 | Sosebee ........................ 128/849 |
| 6,976,451 | B2 | * | 12/2005 | Helfman ....................... 604/386 |
| 7,096,870 | B2 | * | 8/2006 | Lamprich et al. ............. 128/849 |
| 7,543,587 | B2 | * | 6/2009 | Yardan et al. ................. 128/849 |
| 2006/0191540 | A1 | * | 8/2006 | Lamprich et al. ............. 128/849 |

\* cited by examiner

COMBINED DRAPE AND CARRYING BAG UNIT

CROSS-REFERENCE TO RELATED APPLICATIONS

This application is a National Phase Application of PCT International Application No. PCT/US2008/074395, International Filing Date Aug. 27, 2008, claiming priority of U.S. Provisional Patent Applications No. 60/967,018, filed Aug. 31, 2007, and No. 61/052,594, filed May 12, 2008, which are all incorporated herein by reference.

BACKGROUND OF THE INVENTION

1. Field of the Invention

The invention generally relates to the use of a disposable absorbent article in covering medical carts for medical applications used in medical procedure rooms, and in particular to a drape for use in conjunction with endoscopic procedures for containment of waste product and equipment protection.

2. Description of the Related Art

Conventional disposable absorbent drapes or pads used in endoscopic procedures may be comprised of a plurality of absorbent and impermeable material layers joined mechanically to produce a sterile mat of given geometry. Said mats are placed upon medical carts for establishment of a sterile work platform to place endoscopic and other medical instruments upon, beneath the patient procedure zone to contain wastes emanating from the procedure due to gravitational flow from the patients body, and such other areas in the procedural region to allow for capture of waste or the establishment of a sterile work surface.

In a conventional absorbent drape, once the procedure is complete, the equipment involved in the procedure, which is now contaminated, is removed from the area by medical personnel. The equipment may be placed in a separate container for transport, or left exposed to the environment and carried to a decontamination/sterilization area for preparation for the next procedural use. The absorbent disposable drapes used in the procedure are gathered by medical personnel and may also be placed in containers or receptacles for proper disposal of biohazard materials.

During removal of the equipment and drapes, medical personnel may be exposed to biohazard materials deposited on the equipment and drapes. Procedures are commonly employed to reduce the level of exposure, but movement or disposal of the equipment and drapes still involves the placement of the affected articles into separate containers, transport or disposal units, and still involves exposure of medical personnel to biohazard materials deposited thereon.

BRIEF SUMMARY OF THE INVENTION

The present invention provides a disposable absorbent drape or pad having none of the shortcomings of the present art. The present invention generally comprises a disposable absorbent drape or pad, to which about the periphery of the pad an annular feature has been applied facilitating the internal positioning within this annulus of a member functioning as a draw cord for gathering and shortening the perimeter of the drape or pad. The draw cord is stored within the annulus and exposed for a portion of the length of the annulus to allow for medical personnel to grasp the draw cord and proceed to pull the draw cord out of the annulus, thereby shortening the perimeter of the drape or pad and causing a gathering of the drape or pad material into a carrying bag.

In a first embodiment, the disposable absorbent drape or pad has an elongated square, or rectangular, shape, and the annulus extends around the rectangular periphery thereof. In a second embodiment, the disposable absorbent drape or pad has an elongated square, or rectangular, shape with rounded sides, and the annulus extends around the periphery thereof. In a third embodiment, the disposable absorbent drape or pad has an elongated octagonal shape, and the annulus extends around the periphery thereof.

Through use of appropriate permeable and impermeable layers within the drape or pad construction, as well as selection and design of the materials for structural properties, a carrying bag is formed through said operation which can support the weight of the endoscopic equipment used in the procedure therein. Through orientation of the permeable and impermeable layers of the drape or pad, containment of the biohazard waste product of the procedure which have been disposed upon the drape or pad, and the contaminated equipment which has been used in the procedure and placed on the same drape or pad, a sterile outer surface of the gathered invention can be used for disposal or transport of the waste materials or contaminated equipment without placement of same into a separate container.

The present invention thereby reduces the biohazard exposure to medical personnel handling these components postprocedure, and also offers simultaneous protection from damage to the endoscopic equipment during transport from the procedural area.

A primary object of the present invention is to provide a combined drape and carrying bag unit that overcomes the shortcomings of prior art devices. These and other aspects, features and advantages of the present invention may be more clearly understood and appreciated from a review of the following detailed description of the disclosed embodiments and by reference to the appended drawings and claims.

BRIEF DESCRIPTION OF THE DRAWINGS

Various other objects, features and attendant advantages of the present invention will become fully appreciated as the same becomes better understood when considered in conjunction with the accompanying drawings, in which like reference features designate the same or similar parts throughout the several views, and wherein.

DETAILED DESCRIPTION OF THE INVENTION

The present invention is directed to the use of a combined drape and carrying bag unit for use as a sterile or non-sterile surface mat during endoscopic procedures and conversion of same through operation of embodied features therein to a carrying bag for the containment of procedural equipment and waste post-procedure. Briefly described the present invention comprises a combination drape and carrying bag unit to which includes a singular sheet or plurality of joined or attached sheet of pliable materials, both permeable and impermeable, of size to define a mat to accommodate a working medical procedural area thereon, upon which may be placed in single or combination, medical equipment and patient. A drawstring casing extends about the periphery of the drape and has a plurality of openings therein. A drawstring is received in the drawstring casing and is of size to extend about the periphery of the drape when it defines a mat. The drawstring is slidably received in the drawstring casing so that when portions of the drawstring are pulled out of the drawstring casing through the openings, the periphery of the drape forms gathers adjacent the casing to permit the periphery to reduce in size and form a carrying bag.

In a first embodiment, the drape has a generally rectangular periphery defined by two generally parallel side edges and two generally parallel end edges, the side edges being longer than and generally perpendicular to the end edges. The drawstring casing has including, but not limited to, two openings positioned proximate the midpoints of those portions of the casing which extend along the end edges. When portions of the drawstring are pulled out of the two openings and such drawstring portions are secured together adjacent the openings, a handle portion is formed. The handle portion is comprised of the drawstring casing, those portions of the drape adjacent the drawstring casing and those portions of the drawstring pulled out of the openings.

The sheets of pliable material preferably comprises a first generally rectangular sheet of permeable fabric, a second generally rectangular sheet of fluid impermeable fabric and a generally rectangular layer of resilient absorbent material secured between the first and second sheets. Plurality and combination of said sheets may be varied to accommodate absorption, sterility, volume, density, and other material properties. When the unit defines a carrying bag, the first sheet forms an interior surface of the carrying bag and the second sheet forms an exterior surface of the carrying bag.

Figure 1:
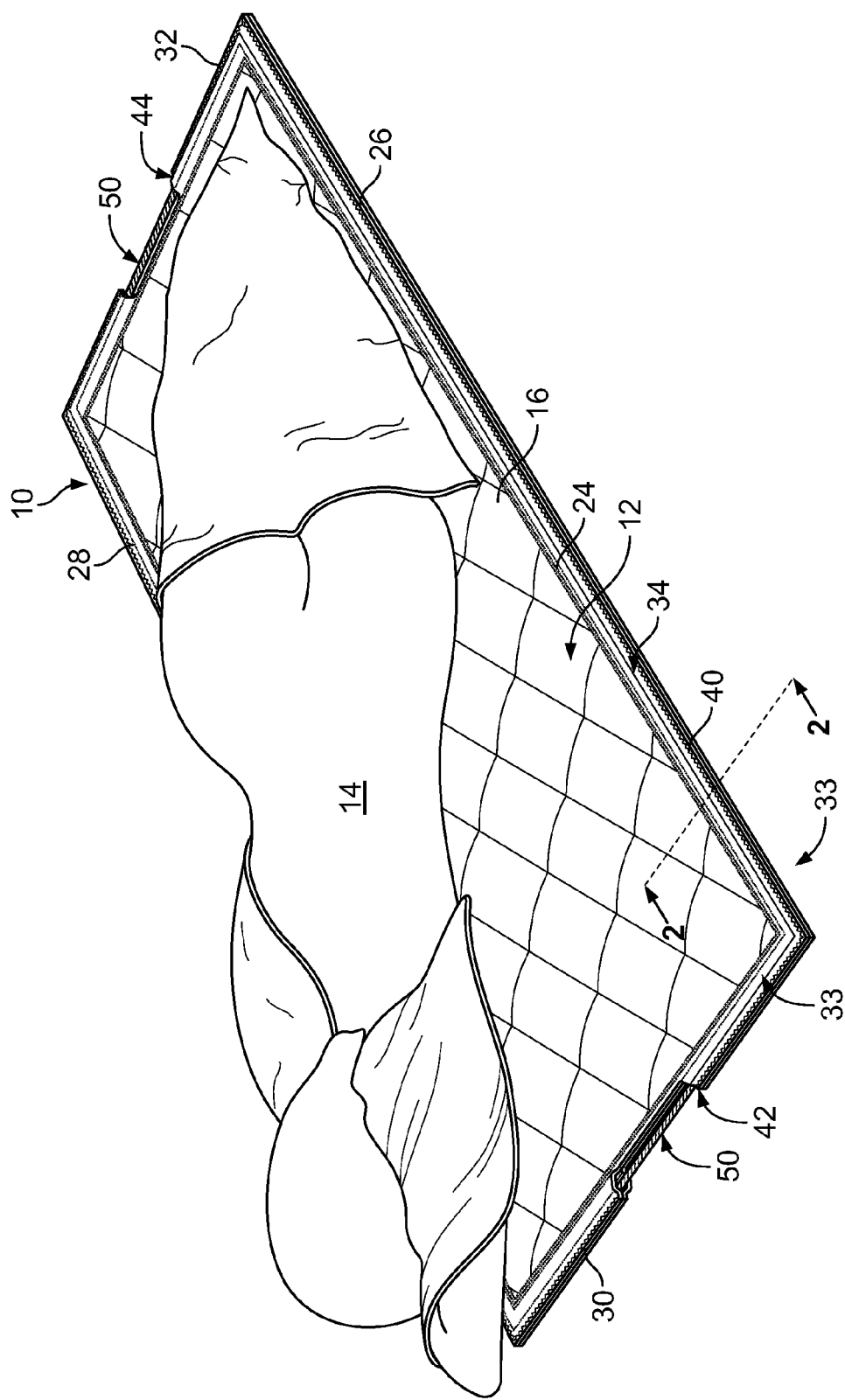
FIG. 1 illustrates perspective view of a typical placement of the combined drape and carrying bag unit of the present invention as it defines a mat for the capture of procedural waste products relative to a patient in a hospital procedure room undergoing an endoscopic procedure.
Figure 2:
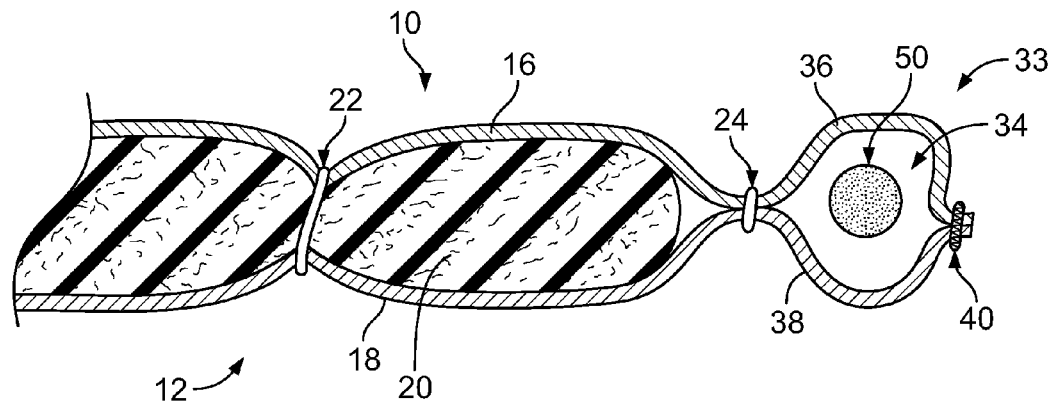
FIG. 2 illustrates a partial sectional view taken along lines 2-2 in FIG. 1.

A combined drape and carrying bag unit 10 of the present invention is shown in use as a mat 12 in FIG. 1. The mat 12 is of size to accommodate a patient's procedural volume 14 thereon and is suitable for use as a sterile or non-sterile procedural mat, medical cart mat, prep area mat, or the like. As shown in FIG. 2, the unit 10 is preferably comprised of a first sheet of permeable pliable fabric 16, a second sheet of impermeable pliable fabric 18 and a layer of resilient absorbent material 20 which is secured between the first and second sheets 16 and 18. First sheet of pliable fabric 16 preferably comprises a layer of woven material, which is soft and pliable enough to be comfortable against the skin of a person 14 using the mat, satisfies procedural sterility requirements, and is durable enough to withstand procedural structural and biological demands. The layer of absorbent material 20 is typically of sterile fluid retention capable medical fiber, and is held generally in place between the first and second sheets 16 and 18 by stitching or quilting the sheets and cushioning material together using sterile joining practices for medical mats as illustrated at 22 in FIG. 2.

Preferably, the first and second sheets 16 and 18 and the layer of resilient absorbent material 20 are generally rectangular in shape so as to define a uniformly and fully cushioned mat 12, as shown in FIG. 1. As best shown in FIG. 2, the first and second sheets 16 and 18 are secured together about their edges (as at 24 in FIG. 2) so that the layer of absorbent material 20 is fully encased by the first and second sheets 16 and 18. The first sheet 16, second sheet 18 and layer of absorbent material 20 thus combine to form a mat 12 having a generally rectangular periphery. The periphery of the mat 12 is defined by two generally parallel side edges 26 and 28 and two generally parallel end edges 30 and 32, with the side edges 26 and 28 being longer than and generally perpendicular to the end edges 30 and 32.

In certain embodiments (not shown), the layer of resilient absorbent material 20 does not cover the same geometric surface area as do the first and second sheets 16 and 18. For example, the layer of resilient absorbent material 20 may cover only the central portion of mat 12 and leave certain regions closest to the side edges 26 and 28 thereof, or alternatively leave certain regions closest to the end edges 30 and 32 thereof, without the layer of resilient absorbent material 20, i.e., with only the first and second sheets 16 and 18. In another embodiment (not shown), the layer of resilient absorbent material 20 covers only the central area of mat 12 and leaves regions closest to both the side edges 26 and 28 and the end edges 30 and 32 thereof without the layer of resilient absorbent material 20, i.e., with only the first and second sheets 16 and 18. In these embodiments, while mat 12 is generally rectangular in shape, it is not a uniformly cushioned mat 12, as shown in FIG. 1, but rather contains cushioning and absorbency only in its central region or in its central longitudinal or central transverse region.

As illustrated in FIG. 2, a hem 33 extends about the entire periphery of the mat 12 to define a drawstring casing or passageway 34. Preferably, the drawstring casing 34 is formed by outer portions 36 and 38 of the first and second sheets 16 and 18 respectively. Preferably the outer edge portions 36 and 38 are secured together adjacent the periphery of the layer of absorbent cushioning material 20 as at 24 and are sewed or welded together by stitching means as at 40 as illustrated in FIG. 2. With the outer edge portions 36 and 38 of the first and second sheets 16 and 18 thus so secured, the drawstring casing 34 or passageway is formed there-between. Preferably, the outer edge portions 36 and 38 of the first and second sheet 16 and 18 are secured in this manner completely about the peripheries of the sheets 16 and 18, thus creating a drawstring casing 34 extending about the entire periphery of the mat 12.

Figure 5:
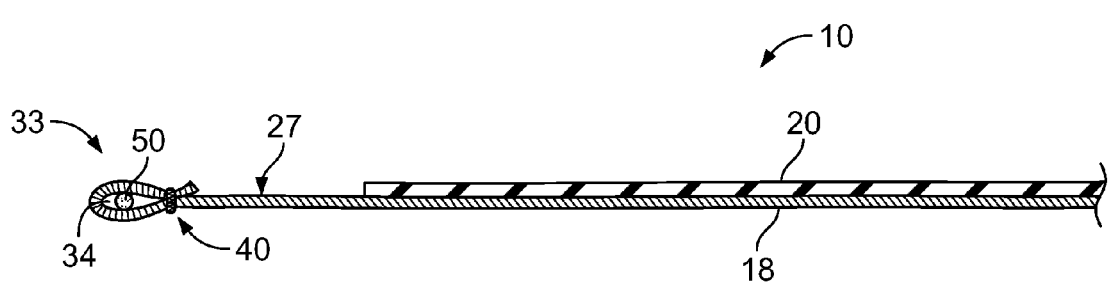
FIG. 5 illustrates a partial sectional view of an alternative embodiment of the combined drape and carrying bag unit.

In a configuration alternative to the configuration shown in FIG. 2, shown in FIG. 5, the unit 10 may be comprised of a sheet of resilient absorbent material 20 that is adhered or bonded to a sheet of impermeable pliable fabric 18. The sheet of absorbent material 20 is typically of sterile fluid retention capable medical fiber. The sheet of absorbent material 20 should also be soft and pliable enough to be comfortable against the skin of a person using the mat 12, satisfy procedural sterility requirements, and be durable enough to withstand procedural structural and biological demands. In this alternative configuration, the sheet of absorbent material 20 is held in place generally against the sheet of impermeable pliable fabric 18 by bonding or adhering with a standard medical grade adhesive, and alternatively also by stitching or quilting the sheets and cushioning material together using sterile joining practices for medical mats.

In certain embodiments, as shown in FIG. 5, the sheet of resilient absorbent material 20 does not cover the same geometric surface area as does the sheet of impermeable pliable fabric 18. For example, the sheet of resilient absorbent material 20 may cover only the central portion of mat 12 and leave certain regions 27 closest to either or both of the side edges 26 and 28 thereof and the end edges 30 and 32 thereof without the sheet of resilient absorbent material 20, i.e., with only the sheet of impermeable pliable fabric 18.

As in FIG. 2, a hem 33 extends about the entire periphery of the mat 12 to define a drawstring casing or passageway 34, which is formed by folding over the peripheral edge of sheet 18 and sewing or welding together the overlapping edge portions of sheet 18 by stitching means as at 40, as illustrated in FIG. 5, thus forming drawstring casing 34 or passageway there-between. Preferably, the overlapping edge portions of sheet 18 is secured in this manner completely about the periphery thereof, thus creating a drawstring casing 34 extending about the entire periphery of the mat 12.

The hem 33 has a first opening 42 and a second opening 44 therein, with each opening communicating with the passageway or drawstring casing 34. The openings 42 and 44 extend through that part of the outer edge portions 36 and 38 which would be otherwise fastened as at 40. The first opening 42 is positioned proximate the midpoint of the end edge 30 of the mat 12 and the second opening 44 is positioned proximate the midpoint of the end edge 32 of the mat 12. The first and second openings 42 and 44 are thus on opposite ends of the mat 12.

Figure 3:
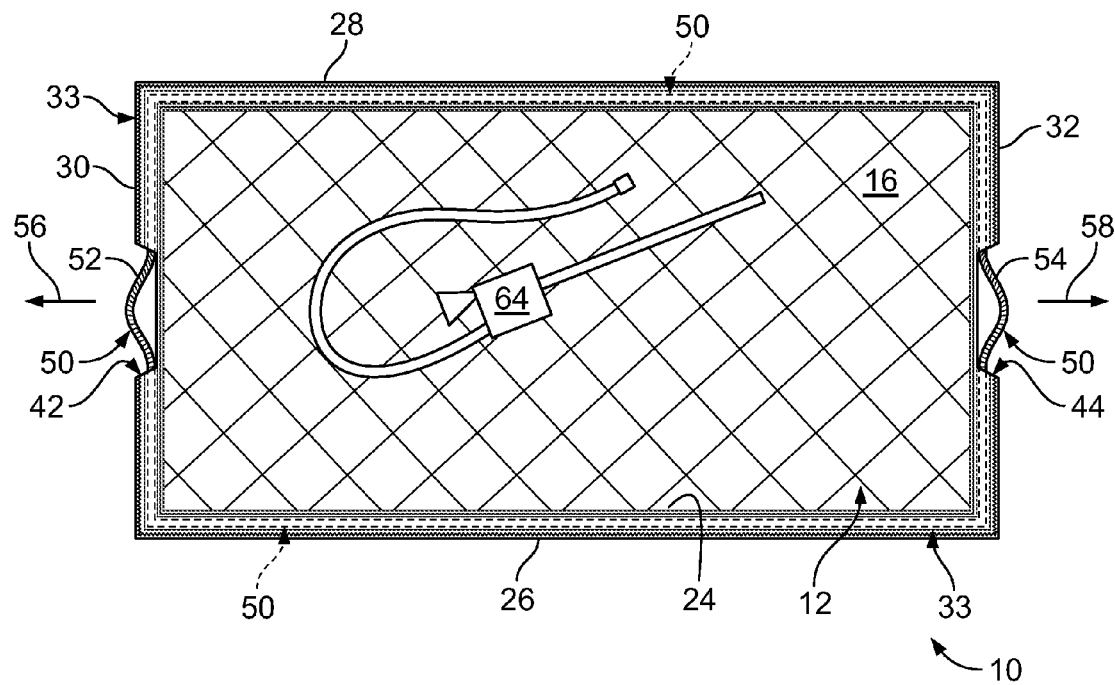
FIG. 3 illustrates a top plan view of a first embodiment of the combined drape and carrying bag unit of the present invention as it defines a mat.

A sterile or non-sterile cord or drawstring 50 is received in the drawstring casing 34 and is of size to extend about the periphery of the unit 10 when it defines a mat 12 as illustrated in FIGS. 1, 3 and 5. The drawstring 50 is slidably received in the drawstring casing 34 so that its movement within the drawstring casing 34 about the periphery of mat 12 is unrestricted. Preferably, the drawstring 50 is endless, with a first portion 52 of the drawstring 50 extending past the first opening 42 of the casing 34 and a second portion 54 of the drawstring 50 extending past the second opening 44 of the casing 34. The first and second portions 52 and 54 are thus always accessible through their respective openings 42 and 44.

In a configuration alternative to the configuration shown in FIG. 3 (not shown), the hem 33 of the mat 12 has first and second openings 42 and 44 therein that communicate with the passageway or drawstring casing 34, as in FIG. 3, but the openings 42 and 44 that extend through that part of the outer edge portions 36 and 38 that would be otherwise fastened as at 40 are positioned proximate the midpoints of the side edges 26 and 28, respectively, of the mat 12, rather than proximate the midpoints of end edges 30 and 32 of the mat 12. The first and second openings 42 and 44 are thus on opposite sides of the mat 12, rather than on opposite ends of the mat 12.

To change the configuration of the unit 10 from a mat to a carrying bag, the first and second portions 52 and 54 of the drawstring 50 are pulled out of the drawstring casing 34 through their respective openings 42 and 44. The drawstring portions 52 and 54 are pulled in direction out of and away from the drawstring casing 34 generally as indicated by arrows 56 and 58, respectively, in FIG. 3.

As the first and second drawstring portions 52 and 54 are pulled out of the openings 42 and 44, the drawstring casing 34, first sheet 16, second sheet 18 and layer of absorbent material 20 form gathers 60 adjacent the periphery of the unit 10 to permit the periphery thereof to reduce in size. The drawing together or contraction of the hem 33 and casing 34 causes the casing 34 to pucker or ruffle to form the gathers 60. The first and second sheets 16 and 18 and layer of resilient absorbent material 20 adjacent the casing 34 also pucker or contract together as the gathers 60 are formed.

Figure 4:
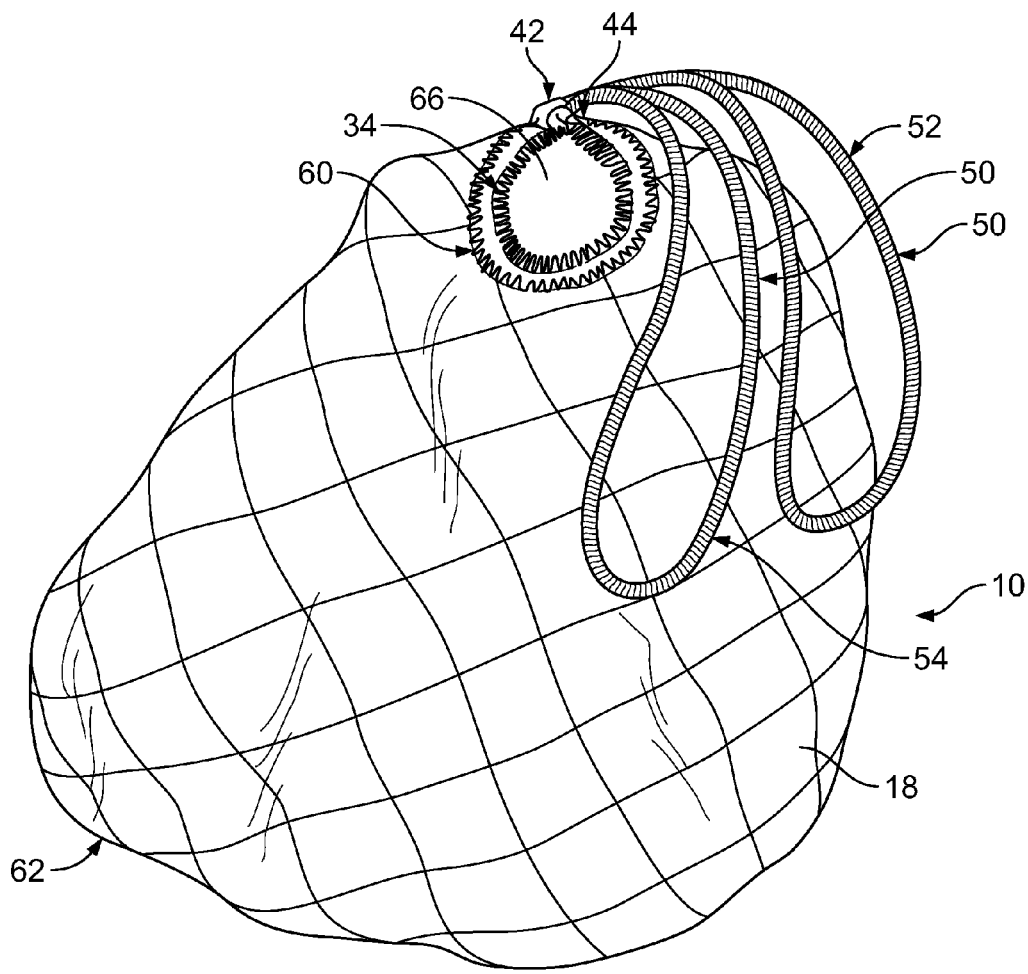
FIG. 4 is a perspective view of the combined drape and carrying bag unit as it defines a carrying bag.

As the periphery reduces in size and the gathers 60 are formed, the edges of the mat 12 are drawn together to cause the unit 10 to form a carrying bag 62. When the unit 10 defines a carrying bag 62 as illustrated in FIG. 4, the first sheet 16 forms an interior surface of the carrying bag 62 and the second sheet 18 forms an exterior surface of the carrying bag 62. When formed as a carrying bag 62 as shown in FIG. 4, procedural equipment and contained procedural waste, such as endoscopic procedure equipment and bodily fluids (designated generally as at 64 in FIG. 3) can be carried within the carrying bag 62. The volume of the carrying bag 62 is dependent upon the size of the mat 12 defined by the unit 10. Because of the pliable nature of the materials comprising the carrying bag 62, it is a highly efficient carrier of materials, capable of defining its shape about the articles to be carried and cushioning the contents therein, and having a large capacity or carrying volume. Also, due to the impermeability and sterility of the second sheet 18 construction, and its facing opposite of the procedural surface first sheet 16, a containment bag for biohazard waste having a sterile or non-sterile outer surface is formed without the use of an external separate containment component having to be employed or the mat and equipment having to be placed within.

A handle portion 66 for the carrying bag 62 is created by securing the drawstring portions 52 and 54 together once they have been pulled out of their respective openings 42 and 44. Preferably, the drawstring portions 52 and 54 are secured together adjacent or proximate to their respective openings 42 and 44 as shown in FIG. 4. The drawstring portions 52 and 54 can be secured together by tying them together or by other suitable fastening means. When the handle portions 52 and 54 are secured together adjacent the openings 42 and 44, the handle portion 66 comprises portions of the sheet adjacent the drawstring casing 34 and portions of the drawstring 50.

When thus formed as a carrying bag 62, the combined drape and carrying bag unit 10 can be easily transported from the procedural area while carrying equipment, waste, or other articles. Because the carrying bag 62 has the layer of resilient absorbent material 20 between its exterior surface and interior surface, the articles carried therein are cushioned and protected from possible damage during transport as a result of the density and padding properties of the combination of sheets. The pliable nature of the carrying bag 62 permits it to take the configuration of the articles being transported as well.

If one were to wish to use the combined drape and carrying bag unit as a sterile or non-sterile receptacle for transport of equipment into the procedural area, one would only have to prepare the invention as described above in the gathered configuration and containing the contents desired to be transported while maintaining appropriate cleanliness. Once in the procedural area, changing the configuration of the combined drape and carrying bag unit 10 from the carrying bag 62 into the mat 12, the drawstring portions 52 and 54 are unsecured or untied and the casing 34 is manipulated (by pulling out the pleats or gathers therein to permit those portions of the drawstring 50 (first and second portions 52 and 54) which are outside of the casing 34 to be slidably received therein. Once the drawstring 50 is fully received within the drawstring casing 34 so that it extends about the periphery of the mat 12 as illustrated in FIGS. 1 and 2, the unit 10 is again suitably configured for use as a sterile drape with any contents of the carrying bag so configured exposed.

Figure 6:
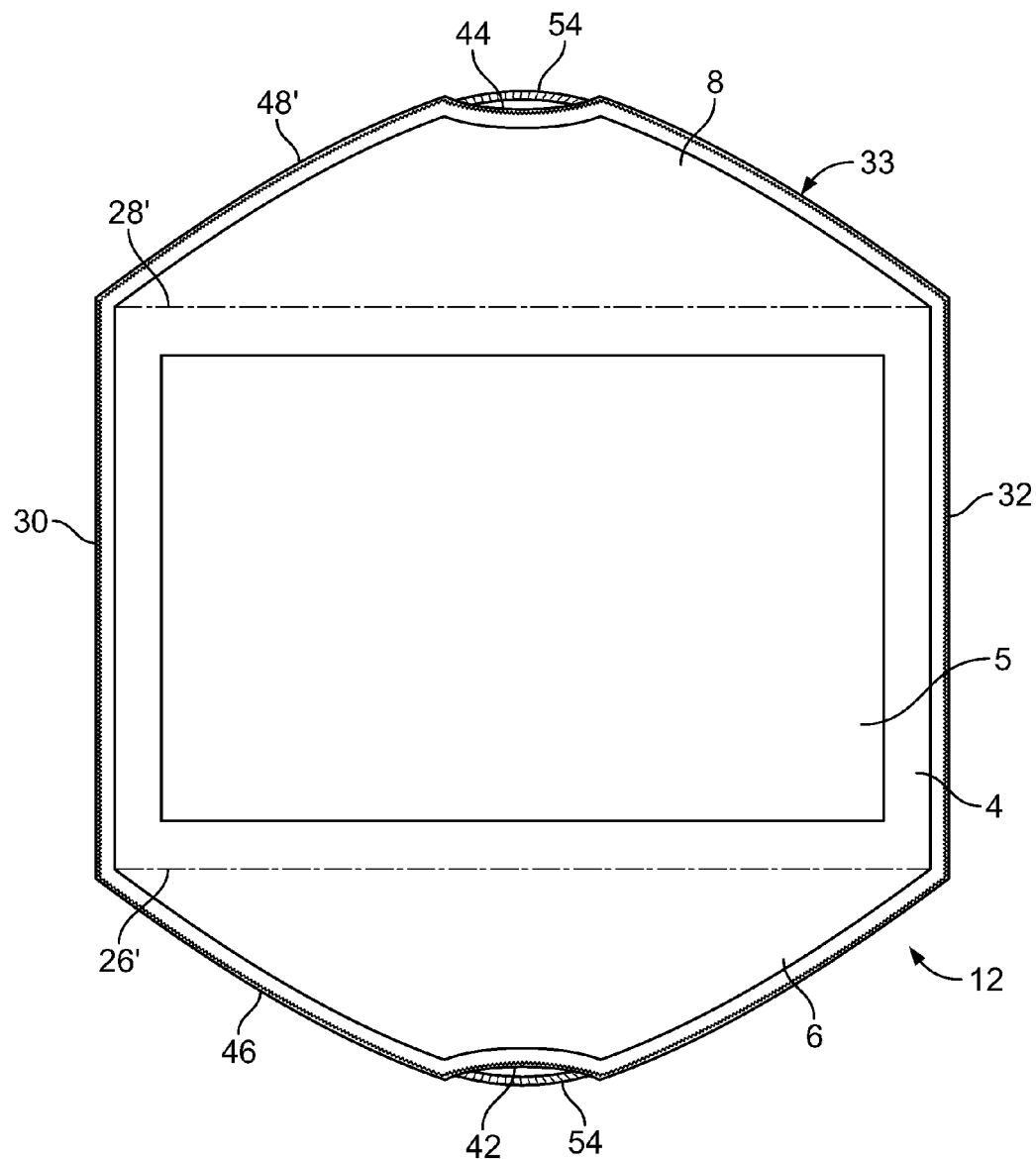
FIG. 6 illustrates a top plan view of a second embodiment of the combined drape and carrying bag unit of the present invention as it defines a mat.

While, in the first embodiment shown in FIGS. 1 and 3, the disposable absorbent drape or pad 12 has an elongated square, or rectangular, shape, and the annulus extends around the rectangular periphery thereof, in a second embodiment, shown in FIG. 6, the disposable absorbent drape or pad 12 has an elongated square, or rectangular, shape with opposing straight end edges 30 and 32 and opposing rounded side edges 46 and 48. In this embodiment, opposing rounded side edges 46 and 48 are generally smooth from end to end, i.e., without sharp changes in the slope therein. Rounded side edges 46 and 48 could be arcuate shaped or could be some modified version thereof, e.g., a crest that is more pointed or more flattened.

As in the other embodiments, the annulus 34 extends around the periphery thereof. As shown in FIG. 6, the layer/sheet of absorbent material 20 and the first and second sheets 16, 18 (or the single sheet 18) combine to form a mat 12 having a generally rectangular central portion 4 defined by two generally parallel nominal side edges 26' and 28' and two generally parallel end edges 30 and 32, with the nominal side edges 26' and 28' being longer than and generally perpendicular to the end edges 30 and 32.

In this embodiment, opposing rounded side edges 46 and 48 extend outward from the nominal side edges 26' and 28' of the pad 12, forming areas 6 and 8, respectively, which appear as opposing side portions or "wings". Areas 6 and 8 provide additional stability and coverage for the medical equipment to be enclosed by pad 12. In a preferred embodiment of FIG. 6, the area 6 of pad 12 that is bound by the rounded side edge 46 and the nominal side edge 26' and the area 8 of pad 12 that is bound by the rounded side edge 48 and the nominal side edge 28' are not equipped with the layer of resilient absorbent material 20, but rather are comprised of only the first and second sheets 16 and 18.

In the embodiment shown in FIG. 6, as discussed in the alternative configuration to FIG. 3 (not shown), the hem 33 of the mat 12 has first and second openings 42 and 44 therein that communicate with the passageway or drawstring casing 34 are positioned proximate the midpoints of the side edges 46 and 48, respectively, of the mat 12, rather than proximate the midpoints of end edges 30 and 32 of the mat 12. The first and second openings 42 and 44 are thus on opposite sides of the mat 12, rather than on opposite ends of the mat 12.

In addition, in the embodiment shown in FIG. 6, the layer of resilient absorbent material 20 may not cover the same geometric surface area as do the first and second sheets 16 and 18. For example, the layer of resilient absorbent material 20 may cover only parts of the generally rectangular central portion 4 of mat 12 defined by the two nominal side edges 26' and 28' and two end edges 30 and 32. In this embodiment, certain regions closest to the nominal side edges 26' and 28' thereof, or alternatively certain regions closest to the end edges 30 and 32 thereof, may be left without the layer of resilient absorbent material 20, i.e., with only the first and second sheets 16 and 18. In another embodiment, shown in FIG. 6, the layer of resilient absorbent material 20 covers only a central area 5 of the generally rectangular central portion 4 of mat 12 defined by the two nominal side edges 26' and 28' and two end edges 30 and 32 and leaves regions closest to both the nominal side edges 26' and 28' and the end edges 30 and 32 thereof without the layer of resilient absorbent material 20, i.e., with only the first and second sheets 16 and 18.

In a configuration of FIG. 6 wherein the unit 10 is comprised of a sheet of resilient absorbent material 20 that is adhered or bonded to a sheet of impermeable pliable fabric 18, the sheet of resilient absorbent material 20 may not cover the same geometric surface area as does the sheet of impermeable pliable fabric 18, as discussed above. For example, the sheet of resilient absorbent material 20 may cover only a central area 5 of the generally rectangular central portion 4 of mat 12 defined by the two nominal side edges 26' and 28' and two end edges 30 and 32 and leave certain regions 27 closest to either or both of the nominal side edges 26' and 28' thereof and the end edges 30 and 32 thereof without the sheet of resilient absorbent material 20, i.e., with only the sheet of impermeable pliable fabric 18, as shown in FIG. 5.

Figure 7:
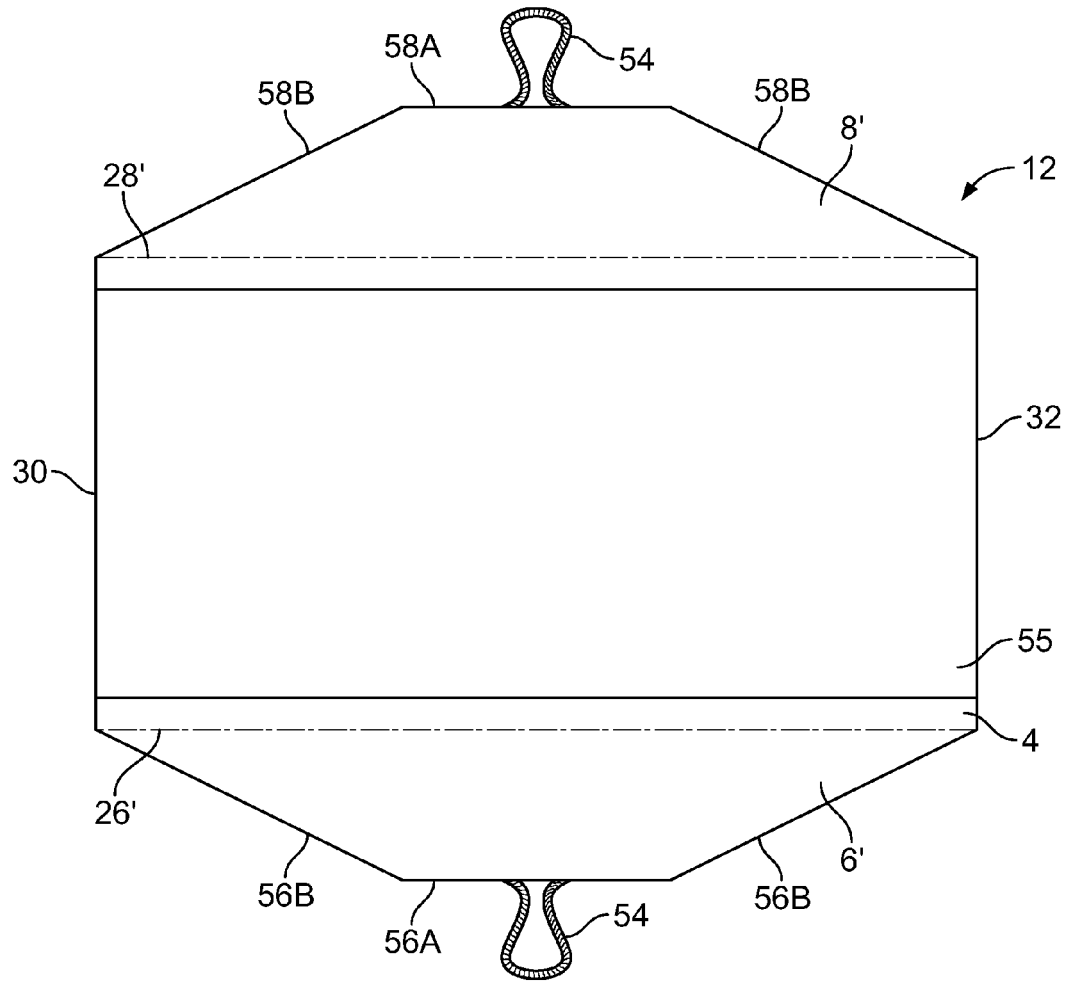
FIG. 7 illustrates a top plan view of a third embodiment of the combined drape and carrying bag unit of the present invention as it defines a mat.

In a third embodiment, shown in FIG. 7, and similar in many respects to FIG. 6, the disposable absorbent drape or pad 12 has an elongated octagonal shape with opposing straight end edges 30 and 32, opposing straight side edges 56A and 58A, and angled corner edges 56B and 58B. In this embodiment, opposing straight side edges 56A and 58A are parallel to each other, as are opposing straight end edges 30 and 32, and opposing side edges 56A and 58A are generally perpendicular to opposing straight end edges 30 and 32. In addition, angled corner edges 56B and 58B may be arranged at any angle less than 180° with respect to end edges 30 and 32 and with respect to side edges 56A and 58A, e.g., smaller angles with respect to end edges 30 and 32 than with respect to side edges 56A and 58A, as shown in FIG. 7, or larger angles with respect to end edges 30 and 32 than with respect to side edges 56A and 58A. Alternatively, angled corner edges 56B and 58B may be arranged at the same angle with respect to end edges 30 and 32 as with respect to side edges 56A and 58A.

As in the other embodiments, the annulus (not shown) extends around the periphery thereof. As shown in FIG. 7, the layer/sheet of absorbent material 20 and the first and second sheets 16, 18 (or the single sheet 18) combine to form a mat 12 having a generally rectangular central portion 4 defined by two generally parallel nominal side edges 26' and 28' and two generally parallel end edges 30 and 32.

In this embodiment, the area 6' of pad 12, bound by the side edge 56A, angled corner edges 56B and the nominal side edge 26', and the area 8' of pad 12, bound by the side edge 58A, angled corner edges 58B and the nominal side edge 28', extend outward from the nominal side edges 26' and 28' of the pad 12, respectively, so as to provide additional stability and coverage for the medical equipment to be enclosed by pad 12. In a preferred embodiment of FIG. 7, area 6' and area 8', which appear as opposing side portions or "wings", are not equipped with the layer/sheet of resilient absorbent material 20, but rather are comprised of only the first and second sheets 16 and 18 or of only the sheet of impermeable pliable fabric 18, as shown in FIG. 5.

In addition, in the embodiment shown in FIG. 7, the layer of resilient absorbent material 20 may cover only parts of the generally rectangular central portion 4 of mat 12 defined by the two nominal side edges 26' and 28' and two end edges 30 and 32, and certain regions closest to the nominal side edges 26' and 28' thereof and/or closest to the end edges 30 and 32 thereof, may be left without the layer of resilient absorbent material 20. In the embodiment shown in FIG. 7, the layer of resilient absorbent material 20 covers only a longitudinally central area 55 of the generally rectangular central portion 4 of mat 12 and leaves regions closest to the nominal side edges 26' and 28' thereof without the layer of resilient absorbent material 20, as discussed above with respect to FIG. 6.

In a preferred embodiment of FIGS. 6 and 7, the width of pad 12 from end edge 30 to end edge 32 is about 41-42 in., the height of pad 12 from rounded side to edge 46 to rounded side edge 48 or from side edge 56A to side edge 58A is about 35-36 in., and the height of pad from nominal side edge 26' to nominal side edge 28' is about 22-23 in. In FIG. 6 the maximum heights of areas 6 and 8 are about 6 in., and in FIG. 7 the maximum heights of areas 6' and 8' are about 7 in. In FIG. 7, the width of opposing straight side edges 56A and 58A is about 14 in.

The central portion 4 of mat 12 defined by the two nominal side edges 26' and 28' and two end edges 30 and 32 is thus about 41-42 in. wide by about 22-23 in. high. In one embodiment, shown in FIG. 6, the area 5 thereof that is equipped or covered with the layer or sheet of resilient absorbent material 20 is about 1½-2 in. from the edges of the central portion, i.e., about 37 in. wide by 17 in. high. In another embodiment, shown in FIG. 7, the area 55 thereof that is equipped or covered with the layer or sheet of resilient absorbent material 20 is about 1½-3 in. from the edges of the central portion, i.e., about 42 in. wide by about 17½ in. high.

Additional alternative embodiments will be apparent to those skilled in the art to which the present invention pertains without departing from its spirit and scope. Use of multiple embodiments of the size, type, shape, and layering of the sheets constructing the mat, as well as number, placement, length, and materials used for the drawstring component allow for suitability of use for various medical applications.

Although the invention has been described in the context of a combined drape and carrying bag unit, the invention includes the use as a medical drape or mat alone wherein post-procedural disposal use of same would eliminate the need for a separate disposal container. Accordingly, the scope of the present invention is described by the appended claims and is supported by the foregoing description.

What is claimed is:

1. A medical equipment pad, comprising:
    a sheet of substantially fluid impermeable material, having
        a substantially longitudinal central region defined by two generally parallel side edges and two generally parallel end edges, wherein each of said side edges is longer than each of said end edges, said central region being of a size to accommodate a patient's procedural volume and an article of medical equipment thereon, and
        two opposing side portions extending outward from the side edges of said central region;
    a sheet of absorbent material attached to said central region of said sheet of fluid impermeable material and not to said opposing side portions, such that said opposing side portions are uncovered by said sheet of absorbent material;
    a drawstring casing extending about a periphery of said sheet of fluid impermeable material and having two openings positioned proximate the midpoints of those portions of the casing which extend along the peripheries of the two opposing side portions of the fluid impermeable sheet; and
    a drawstring received in the drawstring casing and being of a size to extend about the periphery of the sheet of fluid impermeable material, the drawstring being slidably received in the drawstring casing so that when portions of the drawstring are pulled out of the drawstring casing through the two openings, the periphery of the sheet of fluid impermeable material forms gathers adjacent the casing to permit the periphery to reduce in size and to form an enclosure sufficient to enclose the article of medical equipment therein.

2. The pad of claim 1 wherein the sheet of absorbent material is attached between said sheet of fluid impermeable material and a sheet of fluid permeable material.

3. The pad of claim 1 wherein said sheet of absorbent material is adhered or bonded to said sheet of fluid impermeable material.

4. The pad of claim 1 wherein the sheet of fluid impermeable material has a generally rectangular periphery.

5. The pad of claim 1 wherein the sheet of fluid impermeable material has a generally octagonal periphery.

6. The pad of claim 1, wherein said sheet of absorbent material is attached to said central region across at least a majority of the area thereof.

7. The pad of claim 6 wherein said sheet of absorbent material is attached to said central region across only a longitudinal center thereof.

8. The pad of claim 6 wherein said sheet of absorbent material is attached to said central region within an internal portion thereof.

9. The pad of claim 6 wherein said peripheries of the two opposing side portions are rounded.

10. The pad of claim 6 wherein said peripheries of the two opposing side portions comprise corner edges oriented at an angle with respect to both said end edges.

11. The pad of claim 1 wherein, when the periphery of the sheet of fluid impermeable material forms an enclosure, the sheet of absorbent material forms an interior surface of the enclosure and the sheet of fluid impermeable material forms an exterior surface of the enclosure.

12. A method of enclosing and disposing of medical waste or equipment, comprising:
    placing the medical equipment pad according to claim 1 upon a surface, with said sheet of substantially fluid impermeable material in contact with said surface and said sheet of absorbent material exposed upwards;
    placing medical waste or a used article of medical equipment upon the sheet of absorbent material of the medical equipment pad;
    and
    pulling portions of said drawstring out of said drawstring casing through said two openings, thereby forming an enclosure and enclosing therein the medical waste or the used article of medical equipment.

13. The method of claim 12 further comprising placing the medical equipment pad proximal to a medical procedure area.

14. The method of claim 12 whereby the sheet of absorbent material absorbs bodily fluid from said medical waste or said used article of medical equipment.

15. The method of claim 12 whereby the enclosure retains therein bodily fluid from said medical waste or said used article of medical equipment.

* * * * *